US00PP14740P3

(12) United States Plant Patent
Rabin et al.

(10) Patent No.: US PP14,740 P3
(45) Date of Patent: Apr. 27, 2004

(54) GUZMANIA PLANT NAMED 'AMIMOSA'

(50) Latin Name: *Guzmania squarrosa*
Varietal Denomination: Amimosa

(76) Inventors: Mitch Rabin, 19280 SW. 200$^{th}$St., Goulds, FL (US) 33170; Luc Pieters, Koewegstraat 4, 9270 Laarne (BE)

( * ) Notice: Subject to any disclaimer, the term of this patent is extended or adjusted under 35 U.S.C. 154(b) by 0 days.

(21) Appl. No.: 10/230,238

(22) Filed: Aug. 29, 2002

(65) Prior Publication Data

US 2004/0045069 P1 Mar. 4, 2004

(51) Int. Cl.$^{7}$ ..... A01H 5/00
(52) U.S. Cl. ..... Plt./371

(58) Field of Search ..... Plt./371

(56) References Cited

PUBLICATIONS

GTITM UPOVROM Citation for 'Amimosa' as per QZ PBR 010872; May 30, 2001.*

* cited by examiner

*Primary Examiner*—Kent Bell
(74) *Attorney, Agent, or Firm*—Foley & Lardner

(57) ABSTRACT

A new and distinct cultivar of Guzmania plant named 'Amimosa' particularly characterized by bright multi-yellow inflorescence with contrasting red tips and red-green scape bracts; 4–6 branch spikes, each containing approximately 10 flowers; approximately 60 flowers or flower buds present; stiff, leathery, glossy, dark green leaves.

1 Drawing Sheet

Latin name of the genus and species of the plant claimed: *Guzmania squarrosa.*
Variety denomination: 'Amimosa'.

BACKGROUND OF THE INVENTION

The present invention relates to a new and distinct cultivar of Guzmania. A genus within the family bromeliaceae, hereinafter referred to by the cultivar name 'Amimosa'.

The new cultivar was a naturally occurring whole plant mutation discovered among a tissue culture derived group of 'Tutti Frutti', a patened cultivar (U.S. Plant Pat. No. 8,717). Guzmania comprise a genus of over 100 species of herbaceous evergreen perennials suitable for cultivation in home or under glass. Guzmania is native to tropical America. Guzmania are predominantly epiphytic with a few terrestrial species and are native to the tropics.

The species vary in diameter from 7 or 8 inches to 3 or 4 feet and have rosettes of glossy, smooth edged leaves. Floral bracts of Guzmania frequently have brillant colors and may last for many months. The range of flower colors for Guzmania is generally from the yellow through orange but may also include flame red and red purple. White or yellow, tubular, three petalled flowers may also appear on a stem or within the leaf rosette but are usally short lived. Guzmania may be advantageously grown as potted plants for greenhouse or home use.

The plants are shaded from direct sunlight during the spring to autumn period, the central vase-like part of the leaf rosette is normally filled with water.

Leaves of the Guzmania are usually formed as basal rosettes which are stiff and entire and in serveral ranks. Guzmania have terminal spikes or panicles which are often bracted with petals united in a tube about as long as the calyx.

Asexual propagation of Guzmania is frequently done through the use of tissue culture practices. Propagation can also be from off-shoots which are detached from the mother plant, and may be grown in a appropriate soil or bark mixture. The new cultivar 'Amimosa' is a mutation discovered by the inventors, Mitch Rabin and Luc Pieters, in March of 1998. The new cultivar was asexually propagated by off-shoots by the inventors in Laarne, Belgium and Homestead Fla., in July of 1998.

The new variety has also been asexually reproduced at Laarne, belgium, by means of tissue culture. Continuous asexual propagation has demostrated that the combination of characteristics as herin disclosed for the new cultivar 'Amimosa' are firmly fixed and are retained through successive generations of asexual reproduction. The new cultivar reproduces true to type.

BRIEF DESCRIPTION OF THE INVENTION

The following traits have been repeatedly observed and are determined to be basic characteristics of 'Amimosa' which in combination distinguish this Guzmania as a new and distinct cultivar:

1. bright multi-yellow inflorescence with contrasting red tips and red-green scape bracts;
2. 4–6 branch spikes, each containing approximately 10 flowers;
3. approximately 60 flowers or flower buds present;
4. stiff, leathery, glossy, dark green leaves.

Guzmania 'Amimosa' is similar to the patented cultivar 'Tutti Frutti' in all respects, except for the color of the bracts of the inflorescence. Guzmania 'Tutti Frutti' is characterized by it multi-orange color inflorescence. Compared to 'Tutti Frutti', the primary bracts of the new cultivar, Guzmania 'Amimosa' are bright yellow, with contrasting red tips and red-green scape bracts.

Guzmania 'Amimosa' has not been tested under all available environmental conditions and the phenotype may vary with variations in environmental conditions such as temperature, light intensity, day length and humidity without however, any variance in genotype.

BRIEF DESCRIPTION OF THE DRAWING

The accompanying color photographic drawing shows typical characteristics of 'Amimosa' with colors being as true as possible with illustrations of this type.

The photographic drawing shows Guzmania 'Amimosa' at 12 months old, grown from tissue culture and finished in a 15 cm pot. The follow description is taken from the plant illustrated in the photographic drawing.

DETAILED BOTANICAL DESCRIPTION

Guzmania 'Amimosa' was grown in Laarne, Belgium, and in Homestead Fla., in greenhouse conditions which are typical of the industry. Color references are made to The Royal Horticultural Society Colour Chart (R.H.S.), except where colors of ordinary significance are used.

Parentage: Naturally occurring whole plant mutation derived from Guzmania 'Tutti Frutti'.

Propagation: Tissue culture from off shoots.

Plant:

*Form/ growth habit.*—Basal rosette of closely layered strap-like leaves arranged around a short central stem.

*Height.*—Approximately 42 cm–48 cm including inflorescence.

*Diameter.*—Approximately 75 cm–81 cm.

Foliage:

*Leaf size.*—The basal leaves are approximately 43 cm–55 cm long, and 4.5 cm–5.0 cm wide (flattened); at their widest point near the base, the leaves are approximately 8.5 cm wide.

*Leaf shape.*—The leaf blade is ligulate with an acute tip.The leave blade is channeled. The margins are entire; the leaves are curved outward.

*Surface texture.*—The leaf blade is stiff and leathery, with a glossy surface.

*Color.*—The leaves are dark green throughout the foliage; the underside of the leaves are dark green in base color, flushed with purple; the upper surface is darker and greener than but closest to RHS 147A, and the lower surface is RHS 147B, often flushed with RHS 187A and RHS 187B.

*Average number of leaves.*—The plant produces approximately 24 leaves before producing an inflorescence.

*Roots.*—Roots greenish white, changing to brown, wiry with fine laterals.

Bracts:

*Floral bracts.*—Length: The upper-most floral bract is approximately 5 cm long. Width: 1.2 cm. Color: RHS 151A, tinged with 154A marginally, becoming translucent white RHS 155 B at the base (both surfaces). Number: Approximately 29. Margin: Entire. Texture: Leathery, with a glossy surface, shiny, smooth. General shape/Arrangement: The bracts are lanceolate with acute tips, and are arranged in closely spaced vertical ranks along the inflorescence.

*Primary bracts.*—Length: Primary bracts which cover branch spikes are approximately 10 cm–15.5 cm long. Width: 3.5 cm; the base of the primary bracts at the attachment point to the scape is approximately 6.2 cm in width. Color: the color of the largest most colorful primary bracts is yellow RHS 15A to 15B, with fine streaks of red 45C to 45D, becoming green 147C at the base; the tips of the primary bracts are marked with various amounts of red 45C to 45D (both surfaces). Number: Approximately 17. Margin: Entire. Texture: Leathery, with a glossy surface, shiny, smooth. General shape/Arrangement: The bracts are lanceolate with acute tips, and are arranged in closely spaced vertical ranks along the inflorescence.

*Scape bracts.*—Length: Approximately 17 cm to 24 cm. Width: 3.5 cm, the base of the scape bract at the attachment point to the scape is approximately 6 cm wide. Color: The color of the scape bracts is 147A at the tip, with various amounts of 45C to 45D, with 147C at the base (both surfaces). Number: Approximately 7. Margin: Entire. Texture: Leathery, with a glossy surface, shiny, smooth. General shape/ Arrangement: The bracts are lanceolate with acute tips, and are arranged in closely spaced vertical ranks along the inflorescence.

*Scape.*—Height: Approximately 46 cm. Diameter: Approximately 12 mm. Color: 145B to 145C.

Branch spikes: The infloresence contains 4–6 branch spikes which protrude from under primary bracts, each containing approximately 10 flowers. The bracts of the branch spikes are similar in color and dimension to the terminal bracts.

Flowers:

*Borne.*—Terminal in the inflorescence, and in branch spikes.

*Individual flowers.*—Approximately 60 flowers or flower buds present, terminal in the inflorescence concealed under bracts.

*Calyx.*—Gamosepalous, three sepals present approximately 2.4 cm long and 3 mm wide, color RHS 15A (upper surface) and RHS 15B (lower surface).

*Corolla.*—Gameopetalous, three petals present approximately 4.2 cm long and 0.5 cm wide, color yellow RHS 15A to 15B.

*Time of blooming.*—In mature plants, flowering begins approximately 13–16 weeks after induction, at any time of the year.

*Duration of inflorescence.*—The inflorescence will hold its color approximately 6 months; individual flowers last 1 day, and the total duration of flowering is about 12 weeks.

Floral organs:

*Ovary.*—Superior, three locules, 8 mm long, color RHS 145D.

*Style.*— 3.2 cm long, color RHS 145D.

*Stamens.*—Six present, filament approximately 3.2 cm long.

*Anthers.*— 4.6 mm long, color RHS 4D.

Seed characteristics: None observed.

Pest/disease resistance/susceptibility: No observations made to date.

We claim:

1. A new and distinct variety of Guzmania plant named 'Amimosa' as illustrated and described herein.

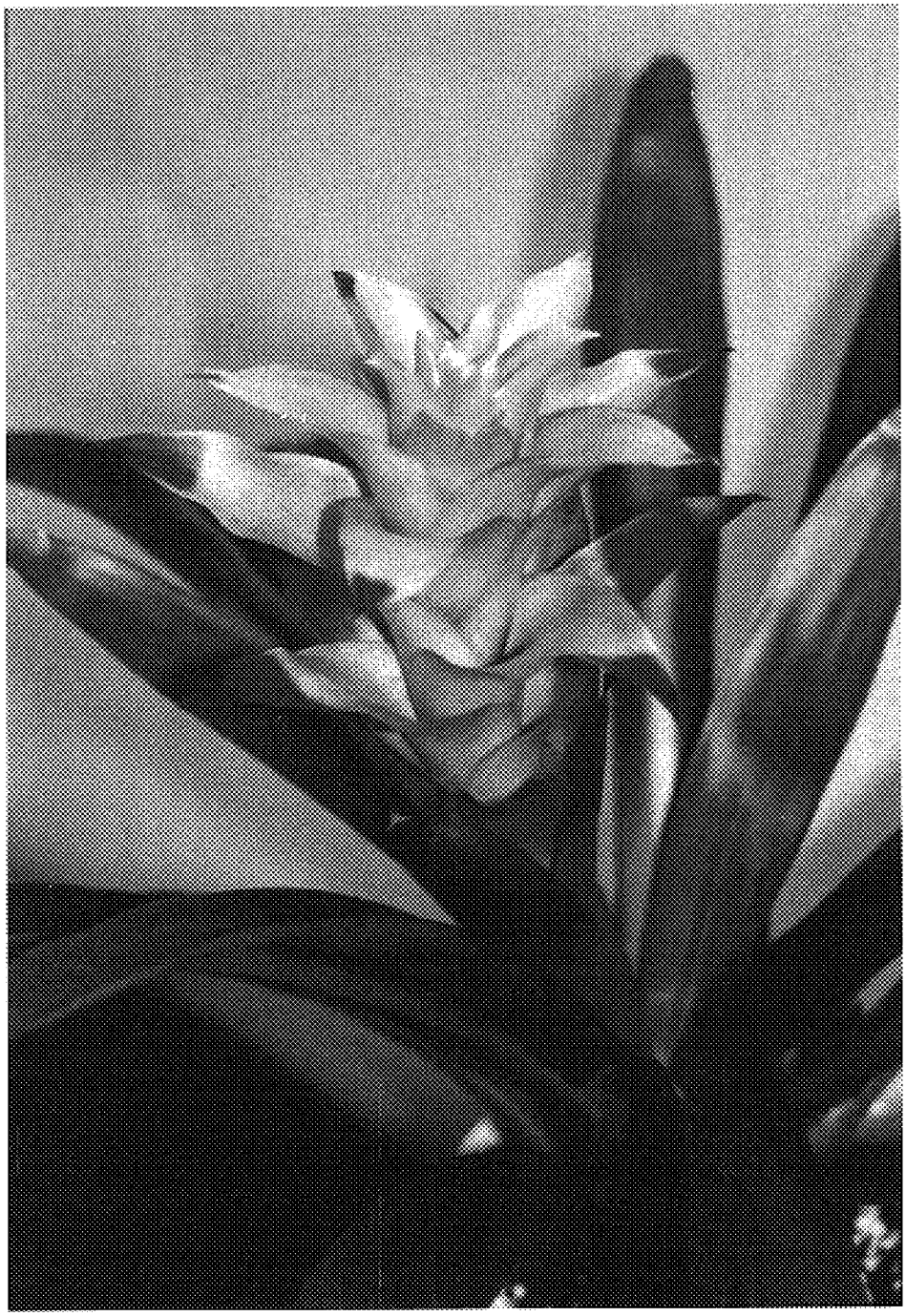

* * * * *